(12) United States Patent
Debreczeny et al.

(10) Patent No.: US 7,079,252 B1
(45) Date of Patent: Jul. 18, 2006

(54) DUAL BEAM FTIR METHODS AND DEVICES FOR USE IN ANALYTE DETECTION IN SAMPLES OF LOW TRANSMISSIVITY

(75) Inventors: Martin P. Debreczeny, Danville, CA (US); Michael P. O'Neil, Sunnyvale, CA (US)

(73) Assignee: LifeScan, Inc., Milpitas, CA (US)

( * ) Notice: Subject to any disclaimer, the term of this patent is extended or adjusted under 35 U.S.C. 154(b) by 777 days.

(21) Appl. No.: 09/586,692

(22) Filed: Jun. 1, 2000

(51) Int. Cl.
*G01B 9/02* (2006.01)

(52) U.S. Cl. ...................................... 356/451
(58) Field of Classification Search .................. 356/451
See application file for complete search history.

(56) References Cited

U.S. PATENT DOCUMENTS

| | | | | |
|---|---|---|---|---|
| 3,753,619 | A | * | 8/1973 | Thorpe et al. ............... 356/451 |
| 4,882,492 | A | | 11/1989 | Schlager |
| 4,999,010 | A | | 3/1991 | Mattson et al. |
| 5,204,532 | A | | 4/1993 | Rosenthal |
| 5,222,496 | A | | 6/1993 | Clarke et al. |
| 5,237,178 | A | | 8/1993 | Rosenthal et al. |
| 5,424,545 | A | | 6/1995 | Block et al. |
| 5,574,283 | A | | 11/1996 | Quintana |
| 5,715,055 | A | * | 2/1998 | Nanko et al. ................ 356/451 |
| 5,830,132 | A | | 11/1998 | Robinson |
| 5,945,676 | A | | 8/1999 | Khalil et al. |
| 5,957,841 | A | | 9/1999 | Maruo et al. |
| 6,002,953 | A | | 12/1999 | Block |
| 6,016,435 | A | | 1/2000 | Maruo et al. |

OTHER PUBLICATIONS

Beduhn et al. (1986), "Advantages of Dual-Beam Interferometry in Fourier Transform Infrared Spectrometry," *Applied Spectrometry*, vol. 40(5):628–632.
Kuehl et al. (Mar. 1978), "Dual-Beam Fourier Transform Infrared Spectrometer," *Analytical Chemistry* vol. 50(3):418–422.
Griffiths et al. (1986), "Fourier Transform Infrared Spectroscopy—Chapter 8 Reduction of Dynamic Range in FT-IR Spectrometry," vol. 83:298–311.
Klonoff, David C. (Mar. 1997), "Noninvasive Blood Glucose Monitoring," *Diabetes Care*, vol. 20(3):433–437.

* cited by examiner

*Primary Examiner*—Samuel A. Turner
(74) *Attorney, Agent, or Firm*—Frank P. Becking; Bozicevic, Field & Francis LLP

(57) ABSTRACT

Methods and devices are provided for determining the presence and/or concentration of at least one analyte in a sample of low transmissivity. In the subject methods, a forward beam and a backward beam are produced by or introduced into an interferometer from at least one infrared radiation source. The forward beam is passed into the sample and then collected to produce a sample beam while the backward beam is passed into a reference and then collected to provide a reference beam. The sample and reference beams are recombined either optically into a null beam which is detected at a single detector or electronically nulled after detection on two separate detectors. The presence, and often amount, of at least one analyte in the sample is then derived from the detected null beam. Also provided are devices for practicing the above methods. The subject methods and devices are suitable for use in a variety of different applications, including the detection of the presence, and amount, of one or more blood analytes in a physiological sample, such as blood, tissue or derivatives thereof.

20 Claims, 9 Drawing Sheets

DUAL BEAM FTIR METHODS AND DEVICES FOR USE IN ANALYTE DETECTION IN SAMPLES OF LOW TRANSMISSIVITY

FIELD OF THE INVENTION

The field of this invention is analyte detection and quantitation.

BACKGROUND OF THE INVENTION

Analyte detection in physiological samples of tissue or fluids, e.g. blood or blood derived products, is of ever increasing importance to today's society. Analyte detection assays find use in a variety of applications, including clinical laboratory testing, home testing, etc., where the results of such testing play a prominent role in diagnosis and management in a variety of disease conditions. Analytes of interest include alcohol, formaldehyde, glucose, glutamic acid, glycerol, beta-hydroxybutyrate, L-lactate, leucine, malic acid, pyruvic acid, steroids, ascorbic acid, acetone and other ketone bodies, folate, ammonia, bilirubin, creatinine, hemoglobins, lipids, phenylalanine, proteins (including albumin andglobulins), triglycerides, urea, as well as pharmaceuticals and drugs of abuse. As such, analyte testing is of increasing importance to today's society.

While the concentration of blood analytes can be monitored in a variety of different ways, of increasing interest are non-invasive methods of monitoring the concentration of blood analytes. For example, because of its importance in the management of diabetes, much research and effort has gone into the development of non-invasive methods and devices for monitoring the concentration of blood glucose.

One type of non-invasive method for measuring blood glucose involves the use of near infra-red spectroscopy, in which light in the near infra-red wavelength region is passed through or reflected from a sample and the emitted signal is used to derive the concentration of analyte in the sample. A number of non-invasive devices for monitoring blood analytes, including blood glucose, with near infra-red spectroscopy are known to those of skill in the art, including those disclosed in the references listed in the relevant literature section, supra.

In order to measure the absorption of light by a sample in discrete wavelength regions of the near infrared spectrum, a method of separating the wavelength contributions is needed. Such methods described in prior art include filter wheels, diffraction-grating-based spectrometers, acousto-optic tunable filters (AOTF) and Fourier transform infrared (FTIR) spectrometers. If the analyte of interest is strongly light-absorbing and easily distinguishable spectroscopically, a filter wheel apparatus may provide enough discrete wavelengths to allow the analyte concentration to be determined. However, in cases, such as glucose in tissue, where the analyte of interest is a weakly absorbing component in a complex mixture, a large number (greater than 10 and more commonly greater than 100) of discrete wavelength regions must be separately analyzed in order to measure the analyte concentration.

In such cases, a diffraction-grating-based, AOTF, or FTIR spectrometer can be used to resolve the spectrum into multiple wavelength regions. In addition to the wavelength resolution of the measurement technique, an important consideration for highly scattering samples such as tissue and blood, is the optical throughput or flux through the spectrometer. In a diffraction-grating-based spectrometer with a single detector element, the throughput of the spectrometer is inversely proportional to the wavelength resolution. Thus, if a large number of wavelength regions are to be resolved, the amount of light reaching the detector will be small. Arrays of detectors may be used to increase the throughput of the spectrometer, but such arrays with high sensitivity to near infrared wavelengths (1–2.5 µm) tend to be expensive. Further, the calibration and drift of the different detector elements in the array becomes a source of inaccuracy in the analyte determination.

In AOTF spectrometers, the individual wavelength regions are separately measured by tuning the filter. Since the entire spectrum is not simultaneously measured, changes in the sample with respect to time can distort the measured spectrum. Further, the necessity of separately measuring the wavelength regions results in a loss in optical throughput compared to techniques that measure the entire spectrum simultaneously.

FTIR spectrometers offer the advantage of high optical throughput combined with high wavelength resolution with the use of a single detector. As a result, for low transmissivity samples (highly scattering and/or strongly absorbing) containing a complex mixture of analytes, FTIR provides an advantage compared to filter-wheel, AOTF, and grating-based spectrometers. While near infra-red FTIR devices and methods show great promise in the field of non-invasive analyte detection, technical hurdles remain to be overcome if such devices are to become commercially viable products. Such technical hurdles include: problems with instrument drift, the need for ultra high precision analog to digital converters, and the like.

As such, there is a continued interest in the development of new devices and methods for near infra-red based analyte concentration detection.

Relevant Literature

Dual Beam Fourier Transform Infrared (DB-FTIR) spectroscopy is described in U.S. Pat. No. 4,999,010, as well as in: Beduhn & White, Applied Spectroscopy (1986) 40: 628–632; Kuehl & Griffiths, Anal. Chem. (March. 1978) 50:418–422 and P. R. Griffiths and J. A. de Haseth, FOURIER TRANSFORM INFRARED SPECTROSCOPY, Chemical Analysis, Vol. 83(1986) John Wiley and Sons, New York, pp 298–311. See also FTIR: FOURIER TRANSFORM INFRARED: A CONSTANTLY EVOLVING TECHNOLOGY, Sean Johnston, Ellis Horwood, N.Y., (1991), pp. 260–274]. Infra-red spectroscopy based non-invasive blood analyte detection protocols are described in U.S. Pat. Nos.: 6,016,435; 6,002,953; 5,957,841; 5,945,676; 5,830,132; 5,574,283; 5,424,545; 5,237,178; 5,222,496; 5,204,532; and 4,882,492; the disclosures of which are herein incorporated by reference; as well as Klonoff, "Noninvasive blood glucose monitoring," Diabetes Care (March, 1997)20(3):433–7.

SUMMARY OF THE INVENTION

Methods and devices are provided for determining the presence and/or concentration of at least one analyte in a sample of low transmissivity. In the subject methods, a forward beam and a backward beam are produced by or introduced into an interferometer from at least one infrared radiation source. The forward beam is passed into the sample and then collected to produce a sample beam while the backward beam is passed into a reference and then collected to provide a reference beam. The sample and reference beams are recombined either optically into a null beam which is detected at a single detector or electronically nulled after detection on two separate detectors. The presence, and often amount, of at least one analyte in the sample is then derived from the detected null beam. Also provided are devices for practicing the above methods. The subject methods and devices are suitable for use in a variety of different applications, including the detection of the presence, and amount, of one or more blood analytes in a physiological sample, such as blood, tissue or derivatives thereof.

DESCRIPTION OF THE SPECIFIC EMBODIMENTS

Figure 1:
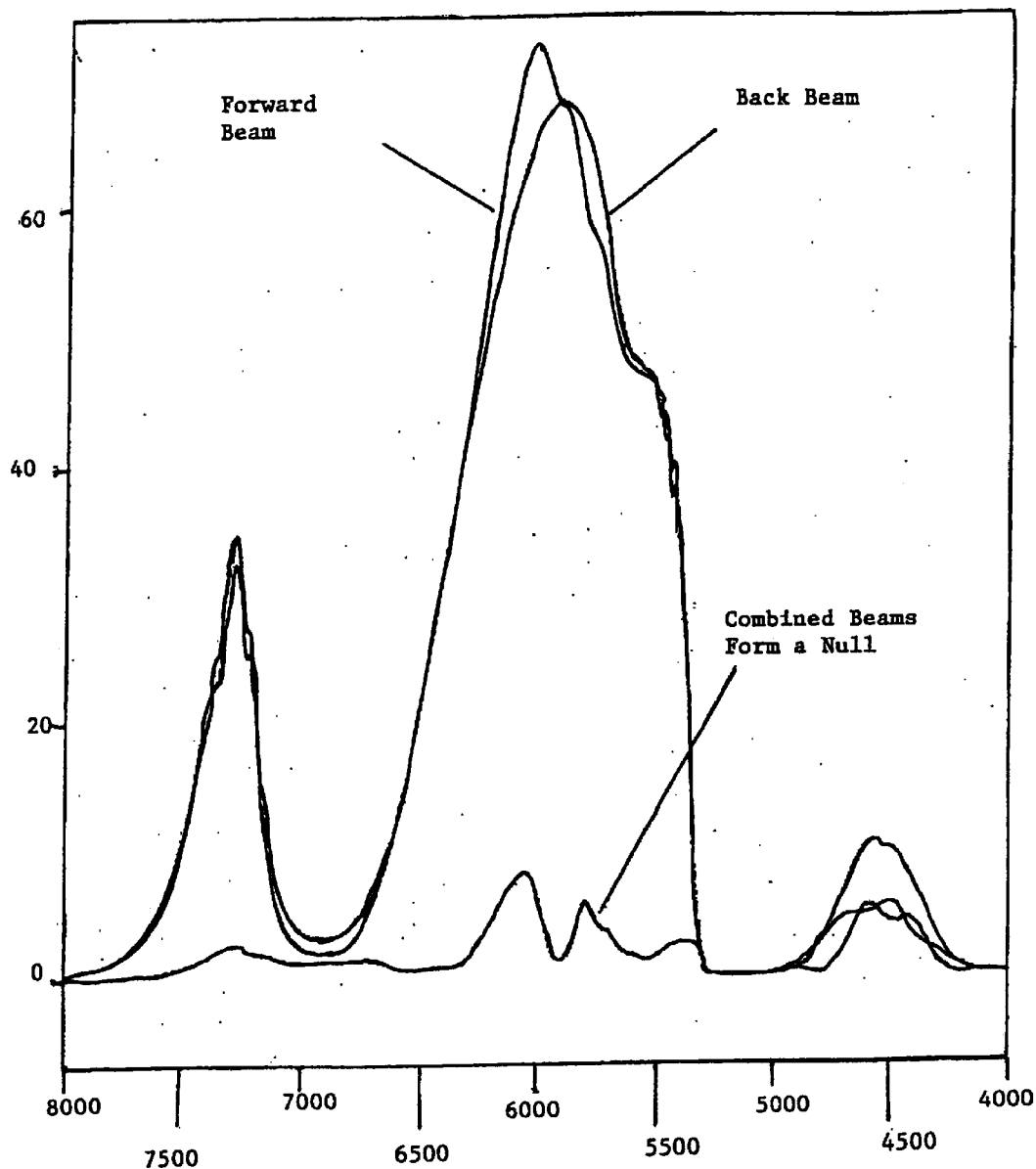
FIG. 1 provides a human forearm diffuse reflectance spectrum (forward beam) and water transmission reference beam (backward beam) and their resulting null.

Methods and devices are provided for determining the presence and/or concentration of at least one analyte in a sample of low transmissivity. In the subject methods, a forward beam and a backward beam are produced by or introduced into an interferometer from at least one infrared radiation source. The forward beam is passed through the sample to produce a sample beam while the backward beam is passed through a reference to provide a reference beam. The sample and reference beams are recombined either optically into a null beam which is detected at a single detector or electronically nulled after detection on two detectors. The presence, and often amount, of at least one analyte in the sample is then derived from the detected null signal. Also provided are devices for practicing the above methods. The subject methods and devices are suitable for use in a variety of different applications, including the detection of the presence, and amount, of one or more blood analytes in a physiological sample, such as blood, tissue or derivatives thereof. In further describing the subject invention, the subject methods will be described first, followed by a review of a representative device of the subject method and a review of various representative applications in which the subject invention finds use.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, singular references include the plural, unless the context clearly dictates otherwise. Unless defined otherwise all technical and scientific terms used herein have the same meaning as commonly understood to one of ordinary skill in the art to which this invention belongs.

Methods

As summarized above, the subject invention provides a method for determining the presence, and often concentration, of at least one analyte in a sample having low transmissivity. Specifically, the subject invention provides a method for determining the presence, and even concentration, of an analyte in a sample using Fourier Transform Infrared (FTIR) spectroscopy. More specifically, the subject methods are dual beam FTIR (DB-FTIR) methods of determining the presence, and concentration, of at least one analyte in a sample of low transmissivity, e.g. glucose in a tissue sample.

In practicing the subject methods, the first step is to produce a forward beam and a backward beam from at least one infrared radiation source, where the forward and backward beams when combined, produce a cancellation (or null) in the a.c. signal and a doubling of the d.c. signal. The infrared radiation employed in the subject methods may be obtained from any convenient source of infrared radiation that is capable of providing radiation in the desired infrared wavelengths, where wavelengths of particular interest are those ranging from, about 0.7 µm to 3 µm, usually from about 1.3 µm to 2.4 µm.

In one embodiment an interferometer is employed to produce the forward and backward beams from an initial, single infrared radiation source. The forward and backward beams are characterized in that, upon leaving or exiting the interferometer, they are exact complements of each other. As such, the backward beam is 180° out of phase with respect to the forward beam upon leaving the interferometer. The forward beam and the reverse beam produced by the interferometer are then passed into a sample and reference, respectively, to produce sample and reference beams.

In an alternative embodiment, two light sources are used to produce the forward and backward beams prior to entering the interferometer. The two light sources may be derived from a single light source by using a beam splitter or similar optical means. The forward and backward beams are then passed into a sample material and reference material, respectively, to produce sample and reference beams. The sample and reference beams are then introduced into an interferometer.

In certain embodiments, the sample into which the forward beam is passed is a low transmissivity sample. By low transmissivity sample is meant that the sample that is characterized by high radiation losses, e.g. radiation losses that exceed about 80%, usually at least about 99% and more usually at least about 99.9%. The low transmissivity samples that may be analyzed according to the subject methods may be samples that are highly absorbing, highly scattering or both.

The subject methods may be used to analyze a variety of different samples. The samples may be naturally occurring or synthetic compositions. Representative samples that may be analyzed according to the subject methods include: industrial products, agricultural products, environmental and waste products, and the like. Specific sample materials of interest include: solid and liquid drug formulations, fine chemicals, plastics, polymers, membranes especially those containing trace analytes of interest such as enzymes, paints and other chemical or physical coatings, liquid products such as petroleum oil and its various distillates including heating oil and gasoline, minerals, natural and synthetic gemstones such as diamond especially when in its powdered form, liquid manufacturing wastes, natural and synthetic fibers, wheat and other grains, milk and dairy products, eggs, meats and other foods, liquid and solid fertilizers, lake and other limnological sediments, and histological specimens. In many embodiments of the subject methods, the sample is a physiological sample. By physiological sample is meant a sample of material that is contained, obtained or derived from a living multicellular organism. In many embodiments, the sample is a tissue sample or derivative thereof. In yet other embodiments, the sample is a physiological fluid sample, e.g. blood, or a derivative thereof. Depending on the particular protocol employed, the sample may be part of or separate from the multicellular organ from which it is derived.

The reference may be any kind of material or composite thereof that provides for a reference beam that nulls at least a portion of, and in many embodiments substantially all of, the non-sample components of the sample beam when the two beams are combined, as described infra. The nature of the reference material or cell may vary greatly depending on the nature of the sample, so long as the above parameters are met. In many embodiments, the reference will be an aqueous composition, where the composition may be pure water, a water solution or a water dispersion. In embodiments where the sample is tissue, the reference may contain pure water or water comprising one or more components that are present in the tissue sample, e.g. metabolites, proteins, lipids, nucleic acids, etc, as well as other scattering components that mimic the scattering qualities of tissue, e.g., an agent(s) that emulates the scattering properties of tissue. In many embodiments in which the sample is tissue, the reference comprises a solid material with water as a major component. Where the reference material is a fluid composition, it is generally present in a suitable containment means. Suitable containment means include those fabricated from silicon, calcium fluoride, infrasil, crystal quartz and the like.

The reference material that is employed in the subject methods may be a fluid contained in a cell having a variable pathlength or a constant pathlength. Where the reference cell has a static or constant pathlength, the pathlength of the reference cell, i.e. the distance that the backward beam traverses as it travels through the reference cell, is generally at least about 5 μm, usually at least about 100 μm and more usually at least about 1 mm, where the distance may be as long as 1 m or longer, but in many embodiments does not exceed about 1 cm and usually does not exceed about 2 mm. Where the reference cell has a variable pathlength, the length of the reference cell is generally adjustable by as much as a magnitude, and in certain embodiments is generally adjustable over a distance of at least about 1 cm, usually at least about 1 mm and more usually at least about 100 μm. As such, the pathlength may be varied by as much as an order of magnitude. However, in many embodiments the pathlength is varied, if at all, by a factor that generally does not exceed about 100%, usually does not exceed about 30% and more usually does not exceed about 10%.

Alternatively, the reference material may be a solid scattering material. The optical scattering and absorption properties of the reference materials may be matched to that of the sample. For samples, such as tissue, the reference material may be a solid with water as a major component, such as gelatin. Another type of reference material may consist of multiple separate materials. For example, the reference beam may be generated by transmitting and reflecting the backward beam through a variety of materials.

In many embodiments, adjustments are made at this point to substantially equalize the energy of the two beams and therefore obtain an optimal null. By substantially equalize the energy of the two beams is meant that various parameters of the device employed in the subject methods are adjusted in order to obtain reference and sample beams that vary in energy by a magnitude of less than about 10%, usually less than about 5% and more usually less than about 2%. By "optimal null" is meant a null in which the nulling ratio is at least about 5:1, usually at least about 20:1 and more usually at least about 50:1, where the nulling ratio may be as high as 200:1 or higher, but typically does not exceed about 50:1. By nulling ratio is meant: the modulated (a.c. component) of the energy present in the forward beam divided by the modulated (a.c. component) of the energy present in the combined beams. Adjustments that may be made to achieve the optimum nulling ratio include: adjustments to the reference cell pathlength and/or adjustments to the overlap of the sample and reference beams upon recombination or collimation into a single null beam, adjustments to the intensity of either the sample or reference beam using a variable attenuator (two examples of variable attenuators that are commonly known in the field: a circular gradient metal-coated attenuator, and a claw attenuator), and adjustments to the composition of the reference material (for example, if the reference cell contains multiple components, a change in the relative concentration of constituents in the reference cell). Where the reference cell pathlength is adjusted, it may be adjusted by as much as an order of magnitude. However, in many embodiments, the magnitude of the adjustment typically does not exceed about 1 mm, usually about 0.5 mm and more usually about 50 microns.

The next step in the subject methods is to detect the null beam(s). In one embodiment, the reference and sample beams are combined at a point prior to the detector into a single beam in a manner sufficient to produce a null beam, where the null beam is characterized in that at least a portion of the non-analyte signal contributions are absent, i.e. they have been canceled out. In general, the beams are recombined using any convenient beam directing means, e.g. reflective means, beam splitter/collimators, fiber optics, etc., into a single null beam. Alternatively, the reference and sample beams may be separately detected and combined electronically. In the two-source embodiment of the subject invention, the reference and sample beams are injected into the forward and backward ports of the interferometer, followed by detection of the output beam(s).

Following detection of the beam(s) at the detector(s), the next step is to derive information regarding the presence (and often amount) of the one or more analytes of interest in the sample. In this derivation step, the detected A.C. signal(s) is(are) generally amplified while the D.C. component of the signal is rejected, the A.C. component of the signal is converted from an analog to digital signal using an AD converter, and the resultant digital signal is processed by the computer to provide information regarding the presence and concentration of analytes present in the sample.

As an alternative to balancing the optical intensity of the two beams on a single detector, the forward and backward beams may be separately detected, and electronically balanced and combined. The electronic signals may combined by using a summing amplifier. In this embodiment it is important that the spectral response of the two detectors be similar, if high null ratios are to be achieved. In yet another embodiment of the present invention, two light sources and two detectors may be used.

The above described methods may be practiced using any convenient device that is capable of providing the requisite forward and backward beams, holding the sample and references of interest, and recombining the reference and sample beams into a null beam. Representative devices which are suitable for use in practicing the subject invention are now described in greater detail below.

Devices

Devices of the subject invention that find use in practicing the subject methods are those that have at least the following components: (a) source(s) of infrared radiation; (b) interferometer means for producing a forward and backward beam or introducing forward and backward beams into the interferometer; (c) a reference material; (d) a sampling apparatus or means, e.g. a holder, or other means depending on the nature of the sample; (e) means for producing a null signal from the reference and sample beams; and (f) detector(s). The device may further include one or more additional components that find use in practicing the subject invention, such as an analog to digital converter (ADC), and a digital data processing or computing means, etc. These elements of the subject device will now be described in greater detail separately and in terms of FIGS. 2 and 3, which schematically depict representative devices according to the subject invention.

Figure 2:
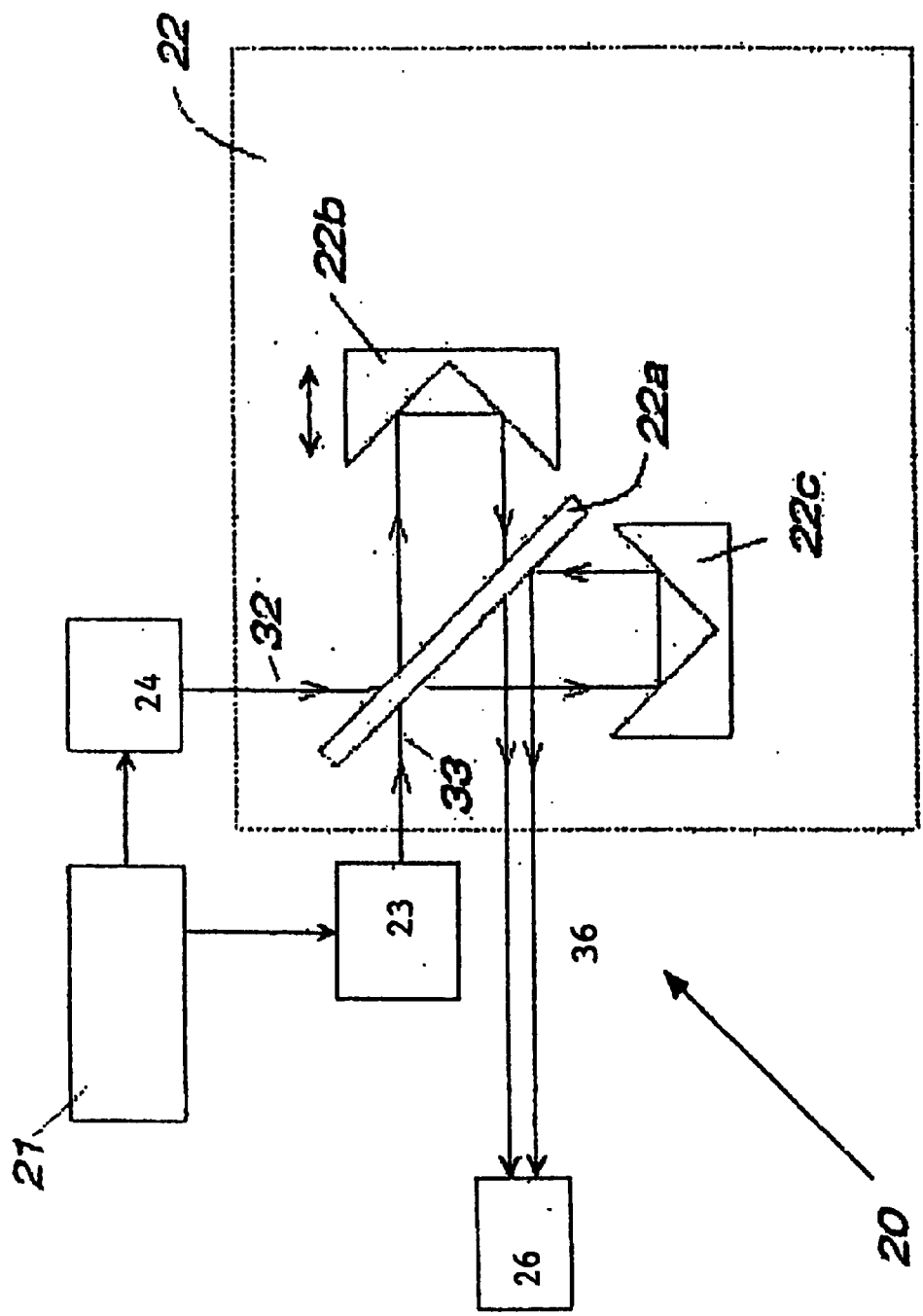
FIG. 2 provides a diagrammatic representation of a device according to the subject invention, of particular use for a sample that interacts with light with strong scattering.
Figure 3:
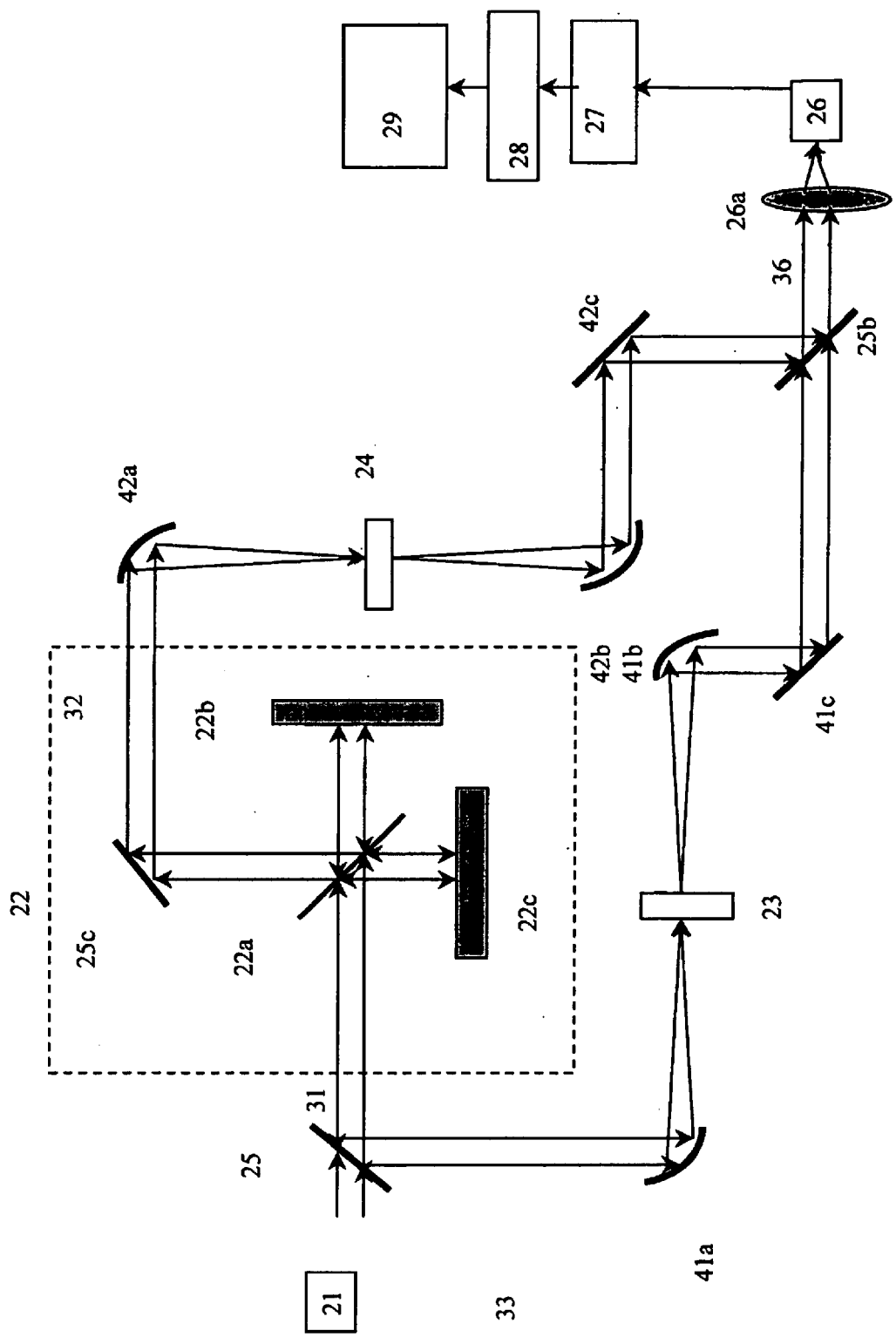
FIG. 3 provides a diagrammatic representation of a device according to the subject invention, of particular use for a sample that interacts with light with weak scattering and strong absorption.

In FIGS. 2 and 3, device 20 includes a source of infrared radiation 21. The infrared radiation source may be any convenient source, including a white light source, a heated filament, a metal carbide rod, etc., so long as it is capable of emitting infrared light having the wavelength spectrum of interest, i.e. light having a wavelength ranging from about 0.7 to 50 microns.

Also present in device 20 is a Michelson interferometer 22, which, in the case of the device in FIG. 2, is capable of accepting a forward 32 and backward beam 33 of light and in the device in FIG. 3 is capable of converting an incident beam of light 31 from the infrared radiation source 21 and converting it into a forward 32 and backward beam 33. The Michelson interferometer typically includes a beam splitter 22a, a moving mirror 22b and a fixed mirror 22c, and optionally additional mirrors for directing the forward beam into or out of the interferometer. Also shown is optical tissue sampler 24, variable path reference 23 and detector 26.

Referring to the device in FIG. 3, the beam splitter 22a of the interferometer 22 produces forward beam 32 and backward beam 33. Forward beam 32 is directed out of the interferometer in one direction while backward beam 33 is directed out of the interferometer along the path of incident light from the radiation source 21. The backward beam is not necessarily overlapping with the path of the incident light. For example, if corner cube optics are used in place of the fixed and moving mirrors in the interferometer, the backward beam path is offset from the path of the path of the incident light. In this case the backward beam can be collected without the need for a beam splitter. This arrangement has the advantage that no incident light is lost in the collection of the backward beam and the total amount of collected light compared to single beam methods, is doubled. A commercial interferometer that provides corner cube optics for the interferometer mirrors and provides easy access to the backward beam is the Bomem Model MB-100. Any convenient interferometer may be employed, where suitable interferometers include: the interferometer found in the Perkin-Elmer 2000, FTIR spectrometer, and the like.

Still referring to the device diagrammed in FIG. 3, a beam splitter 25 is placed in the radiation source incident beam which coincides with the backward beam as it exits the interferometer. The beam splitter is sufficient to redirect a portion of the backward beam out of the incident light path so that at least a portion of the backward beam exiting the interferometer can be directed through a variable path length reference cell 23. Typically, the beam splitter 25 is a 3% reflector, usually at least a 1% reflector, where the beam splitter may reflect up to about 50% or higher, but generally does not exceed about 50%. Any convenient beam splitter may be employed, such as uncoated $CaF_2$, partially metallized, glass or quartz, and the like. The redirected portion of the backward beam is then directed, using any convenient means such as reflectors, mirrors etc., to a reference material.

The variable pathlength reference cell 23 is, in many embodiments, a variable pathlength water cell, where the aqueous composition present in the reference cell may or may not include additional components, e.g. proteins, lipids, metabolites, sugars, etc., as desired. A representative example of a variable pathlength water cell that may be present in the subject device is a variable path length transmission water cell fitted with calcium fluoride, windows. A reference beam 34 emerges from the variable pathlength reference cell. The backward beam and reference beam are directed through use of parabolic reflectors 41a and 41b and mirror 41c.

Ideally the optical properties of the reference material will closely match the optical properties of the sample. For example, in the case where the sample is tissue, the backward beam may be directed into a highly scattering reference material from which diffusely reflected light is collected and used as the reference beam. In addition to being highly scattering, the reference material may contain absorption features that are similar to water, and may also contain other absorption features such as those due to collagen, elastin and lipids to further match the tissue properties. A gelatinous material containing water, collagen, and possibly other materials may serve as a suitable reference material. For an optimal match, the water and collagen content as well as other components of the reference material may be adjusted to match the particular tissue sample being examined.

An alternate method of matching the optical properties of the reference material to that of a complex sample such as tissue is to transmit and/or reflect the backward beam through multiple materials. For example, the backward beam could be transmitted through two variable path length cells, one containing water and another containing lipid in water followed by reflection and collection of the diffusely reflected light from a scattering material. The path length of the water and lipid-containing transmission cells could be adjusted to match the optical properties of the sample.

The forward beam 32, after being directed by beam splitter 25c, is directed by a parabolic reflector 42 from the interferometer to the sample holder 24 which contains the sample to be analyzed. The sample holder may vary depending on the nature of the sample to be contained therein and the nature of the reference employed. Any convenient sample holder configuration made out of any convenient material may be employed. In many embodiments, the sample holder is a tissue sample holder or means for directing the forward beam to a tissue sample. A sample beam 35 emerges from the sample and is directed by parabolic reflector 42*b* and mirror 42*c*.

Fiber optic means are especially well suited to the delivery and collection of light from tissue and other scattering materials. The forward beam is typically focussed onto a single optical fiber or a bundle of fibers such that the focus of the input beam is well matched to the numerical aperture of the fiber or fibers. The fiber material itself should be substantially transparent in the optical region of interest. In order to inject light efficiently, the fiber or bundle of fibers is then brought into close proximity or, preferably, into direct contact with the sample. The injected light is then collected with a separate fiber or bundle of fibers. The collection bundle is typically annular in arrangement, and surrounds the input fiber(s). Alternatively, the collection fiber or bundle may be centrally disposed within an annular ring of input fibers. The input and collection fibers may also be arranged in a random or an ordered grid. As an aide to increase optical throughput, the input or output fibers may be disposed at a non-normal angle with respect to the plane of the sample. An opaque shield may be placed between the input and output fibers and in contact with the sample to prevent light from passing directly from the input to output fibers without first passing through the sample.

As shown in FIG. 3, the reference and sample beams, 34 and 35 respectively, are then recombined at a second beamsplitter 25*b*, which may or may not be the same type of beam splitter as the first beam splitter 25. The beam splitter 25*b* is one that is sufficient to recombine the sample and reference beams to produce a null beam.

Alternatively, the reference and sample beams may be directly recombined on the surface of the detector without a beamsplitter. A convenient method for direct recombination is to bring the reference and sample beams obtained with fiber optic samplers into close proximity or direct contact with the detector. As long as the intensity of the sample and reference beams is well matched, and the detector area is equal to or larger than the area illuminated by the sample and reference fibers, an excellent null can be achieved.

In the device depicted in FIG. 2, the forward and backward beams are generated prior to the interferometer using a single light source and a beam splitter. As with the device depicted in FIG. 3, the forward and backward beams interact optically with the sample and reference materials, respectively, to generate sample and reference beams. However, rather than being recombined after the interferometer as in the device depicted in FIG. 3, the sample and reference beams are now combined within the interferometer, by injecting the two beams into the two ports of a Michelson interferometer.

In the devices depicted in both FIGS. 2 and 3, the emergent null beam 36 is then directed onto detector 26, optionally through a lens 26(*a*) which focuses the null beam onto the detector. The detector is a detector that is capable of converting the incident null beam into an analog signal. Any convenient detector may be employed, where suitable detectors include indium gallium arsenide (InGaAs), indium antimonide (InSb), germanium, and the like.

The A.C. component of the detector-produced analog signal is then amplified while rejecting the D.C. component by an amplifier 27 whose gain is set to fill an analog to digital converter (ADC) 28 also present in the device. Any convenient amplifier may be present in the device, where representative amplifiers of interest include: the AD 797, and the like. The ADC may be any convenient ADC. Because of the nature of the device, the ADC need not be an ultra-high precision ADC. As such, the ADC need only be a 16-bit ADC. The digital output of the ADC is then processed by a data processing means 29, e.g. a computing means, which is capable of taking the digital signal and deriving the presence, and often amount of, analyte present in the sample.

A preferred method of processing the digital signal includes the following steps:

(1) Optional Initial step: subtraction of the dual beam background interferogram measured with a background material in both the forward and backward beams from the dual beam sample interferogram measured with the sample in the forward beam and the background material in the reference beam, resulting in a corrected dual beam sample interferogram.

(2) Fourier transformation of the dual beam sample interferogram (either corrected as in step 1 or uncorrected), resulting in a transformation of the interferogram into a dual beam sample spectrum.

(3) Optional subsequent step contingent on optional initial step 1: Fourier transformation of the single beam sample interferogram measured with the sample in the forward beam and the backward beam blocked, resulting in a single beam sample spectrum.

(4) Computation of the logarithm of the dual beam sample spectrum, resulting in a dual beam sample pseudo-absorbance spectrum.

(5) Optional subsequent step contingent on step 3: Computation of the logarithm of the single beam sample spectrum followed by the subtraction of this spectrum from the dual beam sample pseudo-absorbance spectrum, resulting in a dual beam sample absorbance spectrum.

(6) Multiplication of the absorbance or pseudo-absorbance spectrum by a scaling function, resulting in a scaled absorbance spectrum.

(7) Subtraction of a mean spectrum from the scaled absorbance spectrum, resulting in a mean-centered scaled absorbance spectrum.

(8) Multiplication of each spectral point in the mean-centered scaled absorbance spectrum by a regression coefficient.

(9) Summing the results of step 8 over all spectral points, resulting in a prediction of the analyte concentration in the sample.

The scaling function, mean spectrum, and regression coefficients are determined during a calibration phase. The calibration phase involves measurement of the dual beam FTIR spectra of samples whose analyte concentrations are known. The scaling function, mean spectrum, and regression coefficients are determined in a manner that minimizes the difference between the known analyte concentrations and the analyte concentrations predicted from the dual FTIR spectra. Techniques for accomplishing this are well known in the field and include partial least squares and principal component regression. Both these techniques are discussed in depth in the book "Multivariate Calibration" H. Martens and T. Naes, Wiley and Sons, New York (1989).

The above-described devices may be laboratory scale devices or miniaturized for field use, e.g. doctor's office, home use, etc.

Utility

The subject methods and devices find use in variety of different applications in which the detection of, and determination of the concentration of, one or more analytes in a low transmissive sample is desired. As such, the subject methods and devices find use in the detection of analytes in a wide variety of different types of samples, such as pollutants or toxins in environmental samples, e.g. soil or water, toxins or pathogens in agricultural and food products; detection of impurities in industrial products, and the like. One application of particular interest is the use of the subject methods and devices to detect the presence of one or more blood analytes in an in vivo or ex vivo physiological sample, e.g. blood, tissue or a derivative thereof.

A variety of different analytes may be detected using the subject methods, where representative analytes include: alcohol, formaldehyde, glucose, glutamic acid, glycerol, beta-hydroxybutyrate, L-lactate, leucine, malic acid, pyruvic acid, steroids, ascorbic acid, acetone and other ketone bodies, folate, ammonia, bilirubin, creatinine, hemoglobins, lipids, phenylalanine, proteins (including albumin and globulins), triglycerides, urea, as well as pharmaceuticals and drugs of abuse. While in principle the subject methods may be used to determine the presence, and often concentration, of an analyte in a variety of different physiological samples, such as urine, tears, saliva, and the like, they are particularly suited for use in determining the concentration of an analyte in blood or blood fractions or tissue or tissue fractions. One application of particular interest is the use of the subject methods and compositions to detect the presence of, and determine the amount of, glucose in an in vivo or ex vivo tissue sample.

Detection of the blood analytes according to the subject methods finds use in a variety of different medical applications, including disease diagnosis, disease management, and the like.

The following examples are offered by way of illustration and not by way of limitation.

EXPERIMENTAL

I. Analyte Detection in an Weakly Scattering Aqueous Sample

For a sample that is weakly scattering and strongly absorbing, such as an aqueous solution of analytes (eg. blood serum) interacting with light at near to mid infrared wavelengths, both the forward and backward beams may be employed in transmission mode. As an example, we compared the predictive capabilities of single beam (prior art) and dual beam FTIR for aqueous samples containing three analytes of physiological relevance: creatinine, glucose, and urea.

The instrument configuration used to perform the experiments is diagrammed in FIG. 3. A commercial single beam FTIR spectrometer (Perkin Elmer Spectrum 2000) was modified to function as a dual beam instrument. The instrument was kept open to the atmosphere (21+/−1 C, 40+/−5% RH). A 50% "polka dot" beam splitter (Oriel Instruments, model no. 38106) was used to separate the light source and backward beams. The forward beam was also reflected off of a 50% polka dot beam splitter to equalize the intensity of the two beams. Gold-coated parabolic reflectors focused the forward and backward beams into the sample and reference cells, respectively. The sample and reference cells had a path length of 0.5 mm, as defined by the spacing between their quartz suprasil windows. The temperature of the sample and reference cells was regulated at 22.0 C+/−0.1 C. Gold-coated parabolic reflectors were then used to recollimate the forward and backward beams. The two beams were then combined using a 50% polka dot beam splitter, and focussed onto an InSb detector (7 mm diameter active area, cooled to 77 K) using a silicon lens (2" diameter, approx. 25 mm focal length).

The D.C. component of the signal was removed and the A.C. component was amplified to nearly fill the analog to digital (A/D) converter. The null ratio for this set of experiments was approximately 40:1. Therefore the amplification required to fill the A/D converter with the dual beam signal was approximately 40 times that of the single beam signal. The single beam and dual beam interferograms were interleaved, one after the other for each sample. The spectra were processed according to the procedures (including the optional steps) described already (see section: "DEVICES").

The samples consisted of 27 solutions containing creatinine, urea, and glucose dissolved in water at three concentration levels (creatinine—370, 650, and 930 mg/dL; urea—230, 585, and 940 mg/dL; glucose—0, 250, and 500 mg/dL). The reference cell contained pure water. The complete set of 27 solutions was measured once per day on three separate days. The three measurement days spanned a period of approximately 7 weeks. Samples containing pure water were used as the background samples. Background samples were measured at the beginning and at the end of each set of 27 solutions. The 27 solutions were made up fresh and were measured in a different randomized order on each experimental day.

Figure 4A:
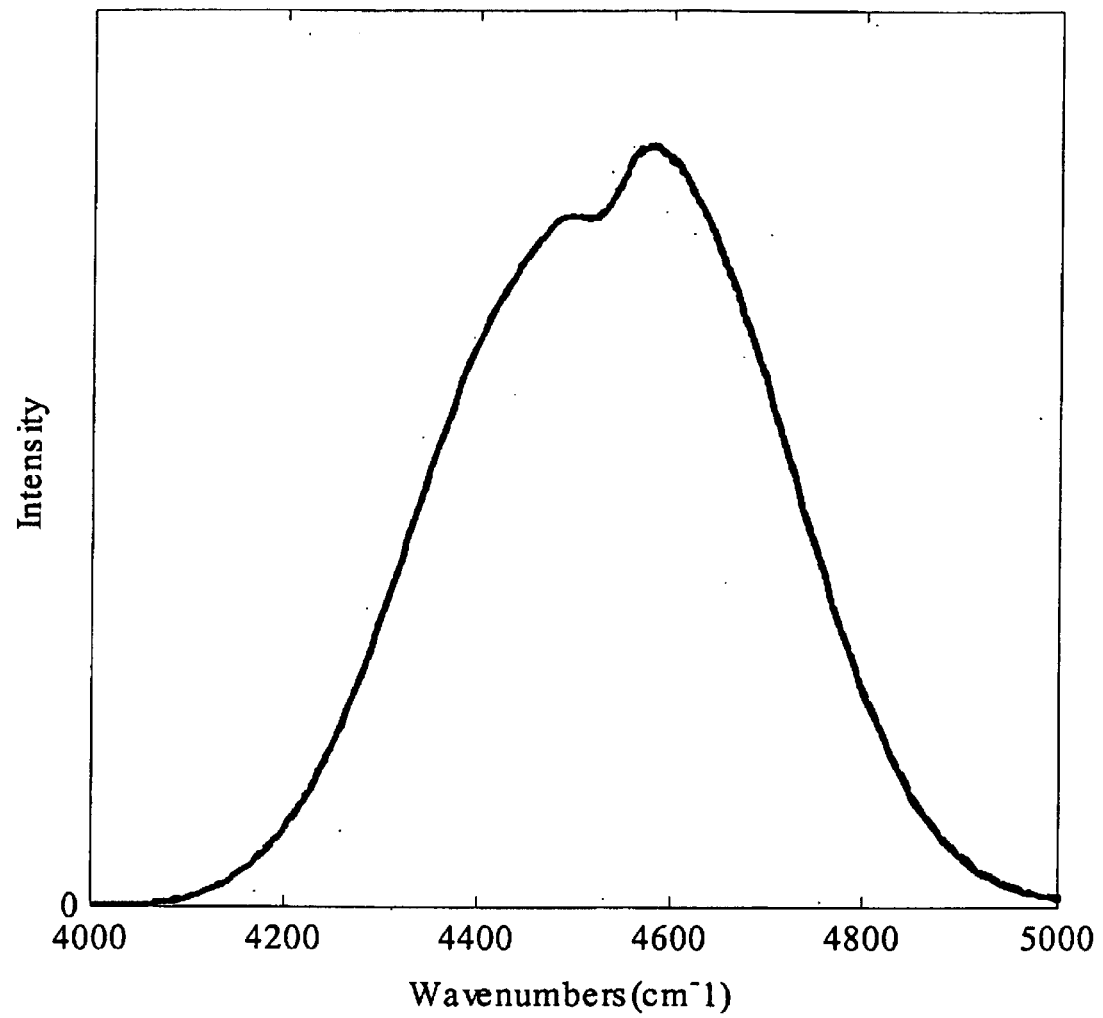
FIGS. 4A and 4B provide spectra of multi-analyte aqueous solutions measured by single beam FTIR (prior art method) and by dual beam FTIR (present invention), respectively.
Figure 4B:
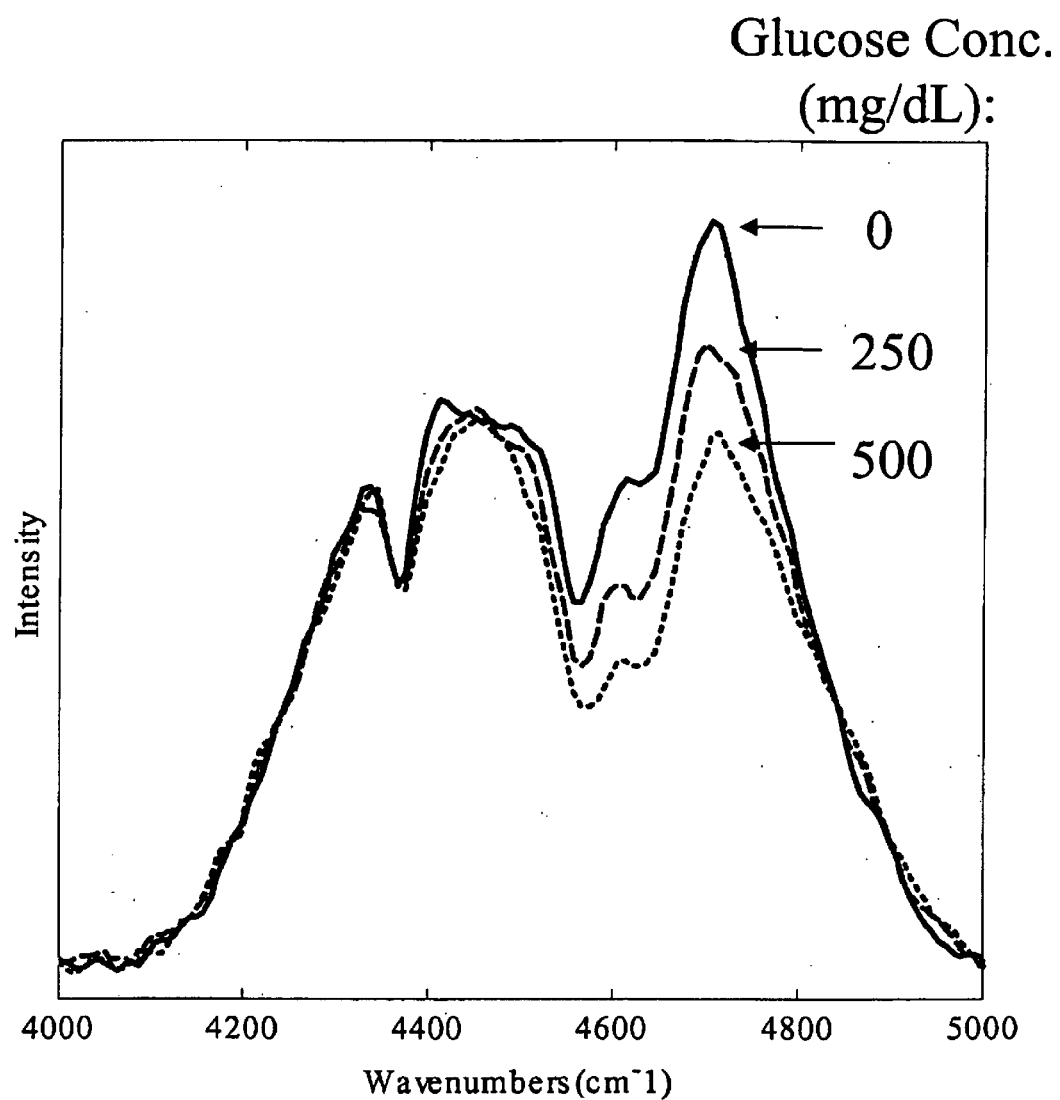

Optical absorption by the three analytes is weak compared to that of water. As a result, the single beam spectra of the 27 samples are nearly indistinguishable by eye. In contrast, the dual beam spectra, from which, by virtue of the optical nulling effect, the lamp emission spectrum and water absorption effects have been largely removed, show clear and obvious spectral changes with changing analyte concentration. FIGS. 4A and 4B show respectively the single beam and dual beam spectra in the 4000–5000 $cm^{-1}$ region of three samples for which the creatinine and urea concentrations are fixed at their lowest levels while the glucose concentration is varied between three levels. The region of maximum spectral change with changing glucose concentration (4700 $cm^{-1}$) corresponds to a known absorption band of glucose in water.

Figure 5:
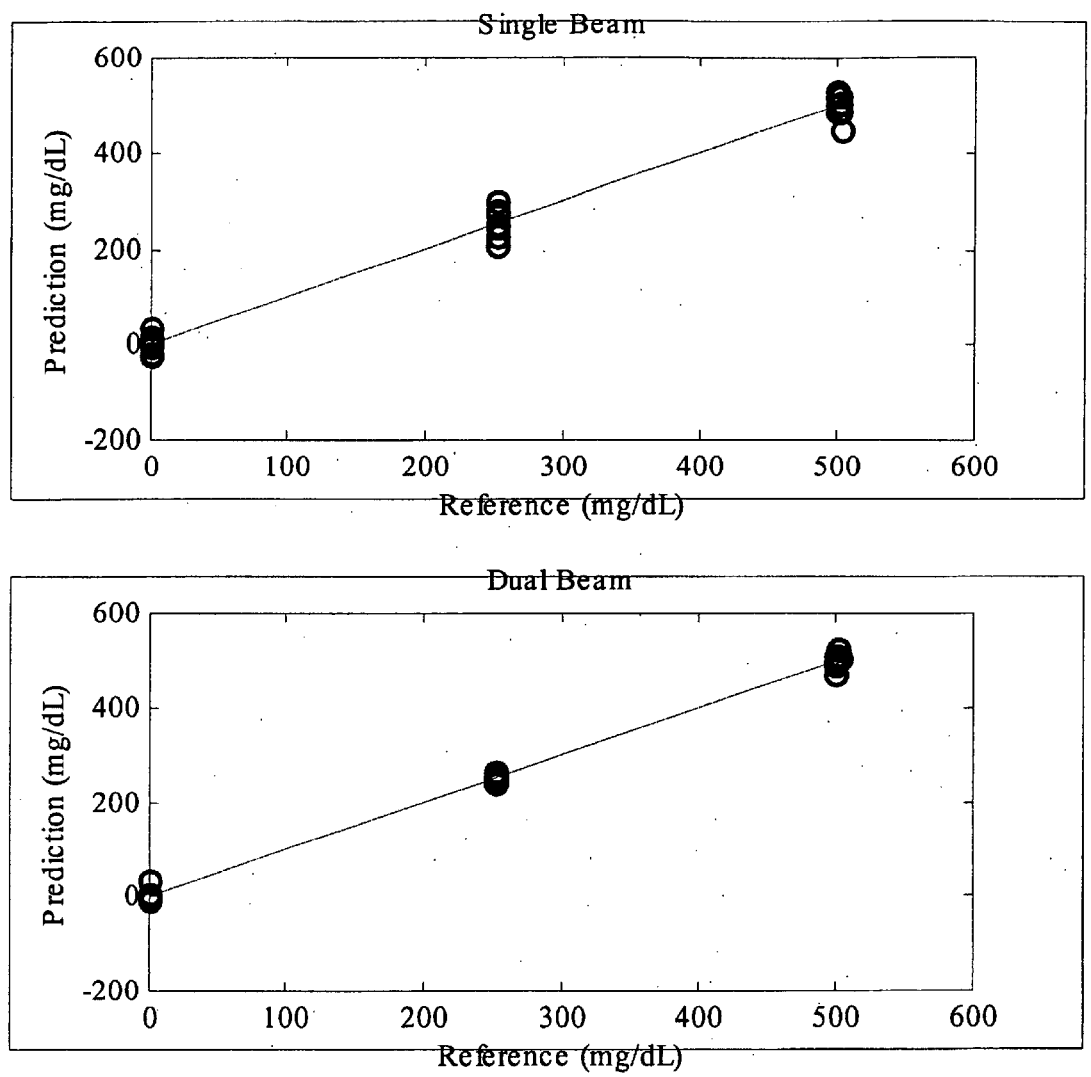
FIG. 5 provides a comparison of predicted and reference glucose concentration in multi-analyte aqueous solutions measured by single beam FTIR (prior art method) and by dual beam FTIR (present invention).
Figure 6:
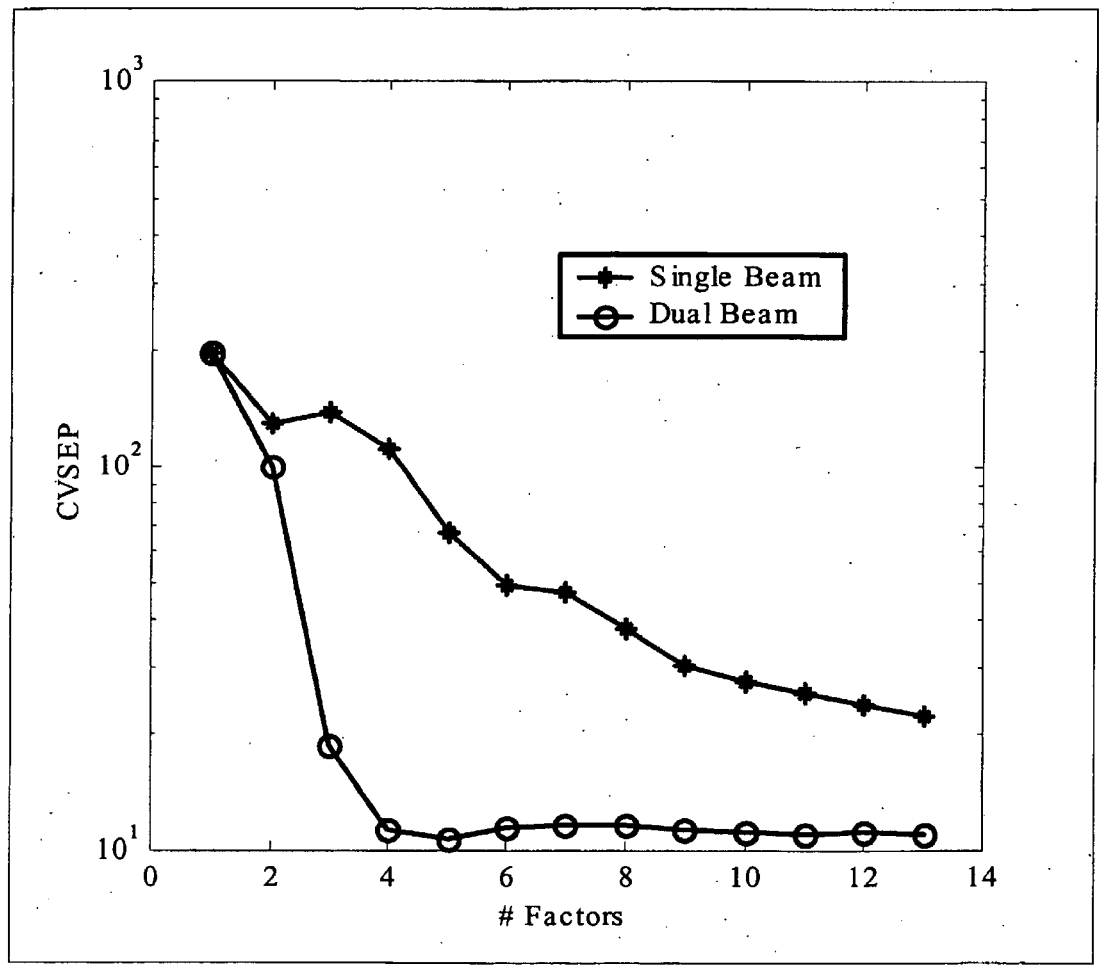
FIG. 6 provides of graphical representation of the standard error of prediction of glucose concentration vs. the number of factors derived from measurements of multi-analyte aqueous solutions by single beam FTIR (prior art) and by dual beam FTIR (present invention) techniques.

Partial Least Squares (PLS) was used to analyze the predictive content of the NIR spectra over the spectral range of 4000–8000 $cm^{-1}$. Analyte predictions within a given experimental day were assessed by choosing a particular sample for prediction and using the remaining 26 samples for calibration. By rotating through all 27 samples in this fashion the "cross-validated" prediction performance was assessed. Predictions of glucose concentration for the spectra acquired in single beam and dual beam mode are compared in FIG. 5. The standard error of prediction (SEP) (i.e., the standard error of prediction is the square root of the average squared difference between predicted and reference concentration) of glucose concentration from the dual beam and single beam spectra is 11.3 and 22.8 mg/dL, respectively. In addition to the improved prediction performance compared to single beam FTIR, the dual beam FTIR calibration model was considerably simpler. This can be seen in a plot of SEP vs. number of factors in the PLS model (FIG. 6). Only 5 factors were used in the best dual beam calibration model whereas at 13 factors the single beam calibration model has still not achieved a minimum SEP value.

Figure 7A:
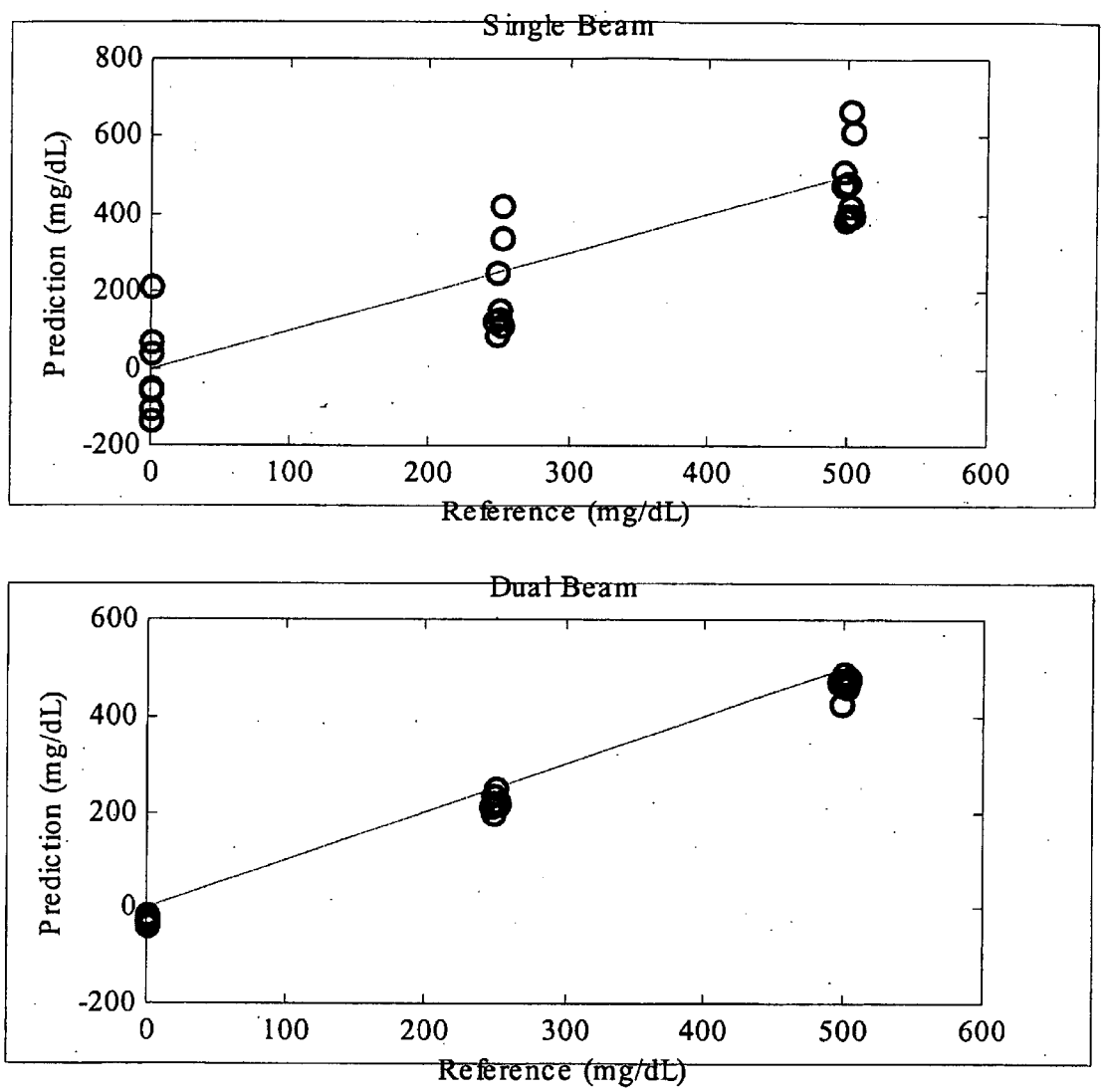
FIGS. 7A and 7B provide a graphical representation of glucose concentration (predicted vs. reference) in multi-analyte solutions measured over the course of several weeks by single beam FTIR (prior art) and by dual beam FTIR (present invention) techniques.
Figure 7B:
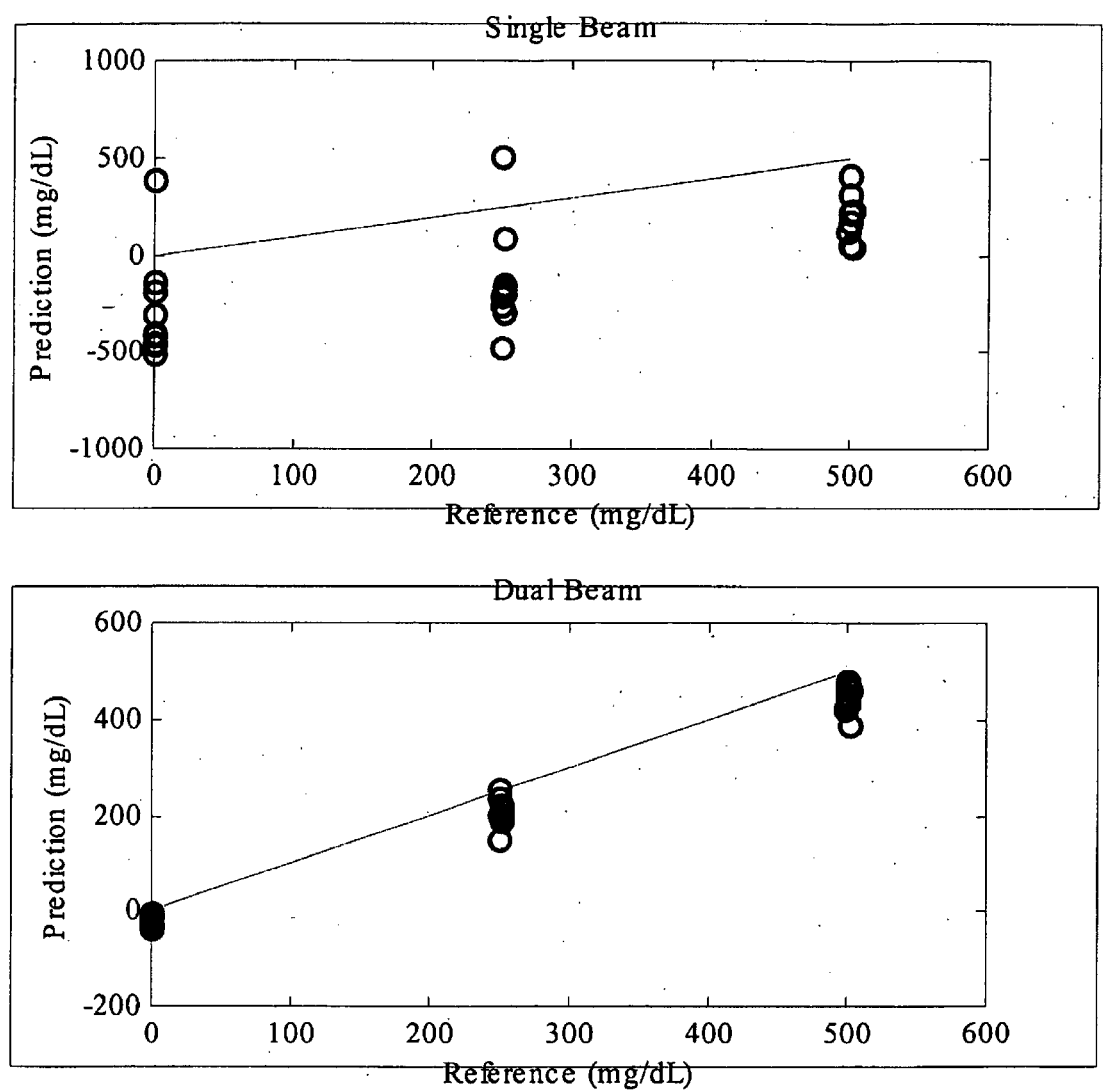

Analyte predictions across multiple days were assessed by using the first day's data as a calibration set and predicting the two subsequent days. The results for the single beam and dual beam techniques at 12 and 4 factors, respectively, are summarized in FIGS. 7A to 7B. In summary, compared to single beam FTIR, the dual beam technique shows better predictive ability of analyte concentration in aqueous solution over both the short (same day) and long term (over 7 weeks).

III. Glucose Detection in Tissue

For a strongly scattering sample that contains a weakly absorbing analyte, such as glucose in mammalian tissue, the forward or sample beam may be employed in reflectance mode whereas the back or reference beam may be in transmission mode.

The instrumental configuration used to perform such a measurement is diagrammed in FIG. 2. A thin calcium fluoride plate may be used to separate the light into forward and backward beams. Since most of the light will be lost in the highly scattering tissue, 96% of the total throughput of the interferometer is used for the forward beam with the remaining 4% used for the back beam which is directed through the reference cell.

The temperature of the reference cells should be regulated at the same temperature as the surface of the tissue being measured since the spectrum of water in the near infra red portion of the spectrum is strongly sensitive to temperature. An attenuator may be used in either or both beams to balance the energy at the detector. The forward beam is focussed with a calcium fluoride lens onto the input of a fiber optic bundle. The bundle directs the forward beam onto, for example, the volar forearm of the human subject being measured. Interleaved with the input fibers at the surface of the tissue are output fibers which direct the scattered and partially absorbed light from the tissue to the detector. Interleaved at the detector with the output fibers are reference (back beam) fibers which direct the light that has passed through the reference cell also onto the detector. The detector is chosen such that its surface area is somewhat larger than the total area illuminated by the interleaved output fiber bundle. The sample and reference beams are thus combined directly at the surface of the detector to form a null.

The D.C. component of the signal is then electronically removed and the A.C. component is electronically amplified to nearly fill the analog to digital (A/D) converter. The null ratio can easily approach approximately 20:1 even though the sample beam, consists of scattered light from the tissue and the reference beam consists of light that has been transmitted substantially without any scatter through a reference cell. The amplification required to fill the A/D converter with the dual beam signal would be approximately 20 fold higher than that of the single beam signal. A calibration is generated by measuring the null spectra of subjects at random but known glucose levels in a analogous fashion with the solution spectra calibration described infra.

It is evident from the above results and discussion that the subject invention provides for an important breakthrough in the use of FTIR for detection of analytes. Specifically, the subject methods and devices overcome prior problems encountered with FTIR determination of glucose in tissue, such as problems with instrument drift, the requirement for use of ultra-high precision ADCs, etc. Importantly, the subject methods and devices are capable of providing highly accurate non-invasive measurements of blood analytes, e.g. glucose. As such, the subject invention represents a significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of determining the concentration of an analyte in a sample of low transmissivity, said method comprising:
    providing a sample of low transmissivity;
    producing a sample beam from said sample of low transmissivity and a reference beam from a reference;
    producing a null signal from said sample and reference beams; and
    deriving the presence of said analyte in said sample of low transmissivity from said null signal.

2. The method according to claim 1, wherein said method comprises using forward and backward beams produced from at least one infrared radiation source to produce said sample and reference beams.

3. The method according to claim 1, wherein said method further comprises passing light through an interferometer.

4. The method according to claim 1, wherein said forward and backward beams are produced from a single infrared radiation source.

5. The method according to claim 1, wherein said forward and backward beams are produced from two infrared radiation sources.

6. A method of determining the concentration of an analyte in a sample of low transmissivity, said method comprising:
    providing a sample of low transmissivity;
    producing a sample beam from said sample of low transmissivity and a reference beam from a reference using forward and backward beams produced from at least one infrared radiation source;
    producing a null signal from said sample and reference beams; and
    deriving the presence of said analyte in said sample of low transmissivity from said null signal;
    wherein each of said beams pass once through an interferometer.

7. The method according to claim 6, wherein said forward and backward beams are produced from a single infrared radiation source.

8. The method according to claim 6, wherein said forward and backward beams are produced from two infrared radiation sources.

9. The method according to claim 6, wherein said null signal is optically produced by combining said sample and reference beams prior to detection at a single detector.

10. The method according to claim 6, wherein said null signal is electronically produced following detection of said sample and reference beams at two separate detectors.

11. The method according to claim 6, wherein said method further comprises:
    producing a forward beam and a backward beam with an interferometer from a single infrared radiation source;
    directing said forward beam into said sample of low transmissivity and directing said backward beam into a reference and collecting a sample beam and a reference beam, respectively;
    combining said sample and reference beams to produce a nulled beam;
    detecting said nulled beam with a single detector to obtain a detected null signal; and
    deriving the presence of said analyte in said sample of low transmissivity from said detected null signal.

12. The method according to claim 6, wherein said method further comprises:
  producing a forward beam and a backward beam from at least one infrared radiation source;
  directing said forward beam through said sample of low transmissivity and directing said backward beam through a reference to produce a sample beam and a reference beam, respectively;
  introducing said sample and reference beams into an interferometer and producing a null signal from said sample and reference beams following their exit from said interferometer; and
  deriving the presence of said analyte in said sample of low transmissivity from said null signal.

13. The method according to claim 6, wherein said sample of low transmissivity is at least one of highly reflective and highly absorptive.

14. The method according to claim 13, wherein said sample is a physiological sample.

15. The method according to claim 14, wherein said physiological sample is selected from the group consisting of blood, tissue or a derivative thereof.

16. The method according to claim 14, wherein said reference comprises water.

17. The method according to claim 16, wherein said reference is a fluid.

18. The method according to claim 16, wherein said reference is a solid.

19. The method according to claim 6, wherein said reference has a variable pathlength.

20. The method according to claim 6, wherein said analyte is glucose.

* * * * *

UNITED STATES PATENT AND TRADEMARK OFFICE
CERTIFICATE OF CORRECTION

PATENT NO. : 7,079,252 B1  
APPLICATION NO. : 09/586692  
DATED : July 18, 2006  
INVENTOR(S) : Marin P. Debreczeny and Michael P. O'Neil It is certified that error appears in the above-identified patent and that said Letters Patent is hereby corrected as shown below:

On Title Page Item (56), under "U.S. PATENT DOCUMENTS" please add:

--U.S. 5,891,619    04-06-1999    Zakim et al  
U.S. 5,440,388     08-08-1995    Erickson  
U.S. 5,178,142     01-12-1993    Harjunmas et al--

On Title Page Item (56), under "References Cited" please add the heading:

--FOREIGN PATENT DOCUMENTS--

On Title Page Item (56), under "FOREIGN PATENT DOCUMENTS" please add:

--0 401 453        12/12/1990    EPO  
DE 19841217        09-09-1998    WO  
WO 99/00660        01-07-1999    WO--

Signed and Sealed this

Tenth Day of April, 2007

JON W. DUDAS  
*Director of the United States Patent and Trademark Office*